April 29, 1941. H. P. READ Plant Pat. 465
SHASTA DAISY
Filed June 25, 1940
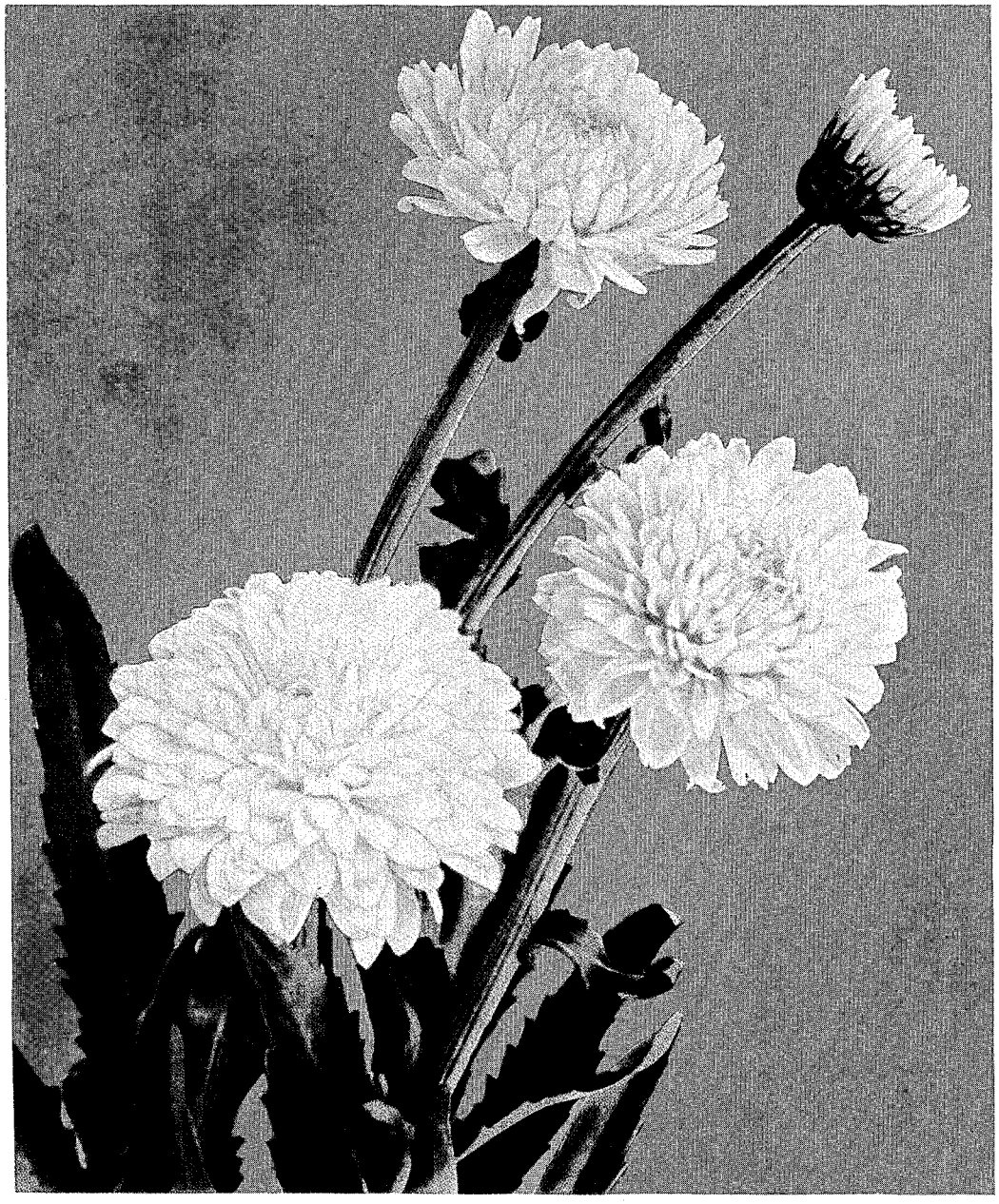
Inventor
H. P. Read
By Robb & Robb
Attorneys Patented Apr. 29, 1941

Plant Pat. 465

UNITED STATES PATENT OFFICE

465

SHASTA DAISY

Horace Postle Read, Brundall, near Norwich, England, assignor to The Conard-Pyle Company, West Grove, Pa.

Application June 25, 1940, Serial No. 342,379

1 Claim. (Cl. 47—60)

The present invention relates to a new and distinct variety of Shasta daisy, particularly desirable for cut-flower-work, as well as for border planting.

This new variety is primarily distinguished in respect to its truly double type of white blossoms, giving to it more the appearance of a true chrysanthemum than is usually found in other daisies belonging to the chrysanthemum family.

Another distinctive feature is its large size, developing from a disc-like bud about one to one and one-half inches to about three and one-half to four inches average in the full blown blossom. As will be observed from the accompanying illustration, the flowers are grown on long, erect, strong stems, similar in this respect to the Esther Reed variety. It differs, however, from that variety in that the latter has a short-petaled pin-cushion center effect, whereas the new variety forms more nearly a ball with long petals, and is tinged with a light greenish color about the center which more or less disappears as the bloom reaches the mature development of an attractive fully double flower borne on stems of generally more than twelve inches in height.

A further feature of distinction is found in the coloring of the foliage of the plant, Yew Green on its face and Cress Green on the back.

Asexual reproduction of the plant shows that these features are established.

The following is a summary or detail description of this new variety, color terminology being in accord with Ridgway's Color Standard where indicated only:

Type: Double Shasta daisy (chrysanthemum family).

*Parentage:* Seedling developed by selection and inbreeding over a period of many years from original *Chrysanthemum leucanthemum* × *Chrysanthemum maximum.*

Flower:

*Locality where grown.*—West Grove, Pennsylvania.

*Flowers borne.*—Singly.

*Quantity of bloom.*—Moderate.

*Continuity.*—Continuous, June until frost.

Bud: Before calyx breaks—

*Size.*—1 to 1½ inches.

*Form.*—Disc, about ⅜″ thick.

Bloom:

*Size when fully open.*—3½ to 4 inches across.

*Petalage.*—Bloom is fully double.

*Form.*—Bomb.

*Fragrance.*—Grass.

*Petalage.*—Approximately 300 or more according to different conditions of cultivation.

Petals: Ribbed.

*Shape.*—Long and narrow.

*Outside petals.*—1¼″ long by ⅜″ broad.

*Inner petals.*—⅝″ long by ¼″ broad.

*Color.*—White throughout.

*Lasting quality.*—About six weeks on plant and almost as long when cut therefrom.

Plant:

*Stem.*—Stiff, 12 to 18 inches high.

*Foliage.*—Leathery, lanceolate, dentate.

*Color.*—On front—Yew Green, Plate XXXI; on back—Cress Green, Plate XXXI.

Growth: Clump growing close to the ground from which the stiff bloom stems rise to height of about three feet. At close intervals on main stem arise numerous branches to form a more or less regularly shaped pyramid, every branch bearing a large white globular shaped flower. These are so numerous that the foliage is almost hidden.

I claim:

A new and distinct variety of Shasta daisy characterized as to novelty by the color of its foliage and the large size fully double form of blossom borne on single stout stems, said flower being white in color tinged at the center with light green until mature when said green disappears, substantially as shown and described.

HORACE POSTLE READ.